(12) United States Patent
Kitagawa et al.

(10) Patent No.: US 9,144,601 B2
(45) Date of Patent: Sep. 29, 2015

(54) SKELETAL MUSCLE REGENERATION PROMOTER

(71) Applicant: SEIKAGAKU CORPORATION, Tokyo (JP)

(72) Inventors: Hiroshi Kitagawa, Kobe (JP); Tadahisa Mikami, Hyogo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 0 days.

(21) Appl. No.: 14/343,960

(22) PCT Filed: Sep. 18, 2012

(86) PCT No.: PCT/JP2012/073794
§ 371 (c)(1),
(2) Date: Mar. 10, 2014

(87) PCT Pub. No.: WO2013/039244
PCT Pub. Date: Mar. 21, 2013

(65) Prior Publication Data
US 2014/0234286 A1 Aug. 21, 2014

(30) Foreign Application Priority Data

Sep. 15, 2011 (JP) ................. 2011-202470

(51) Int. Cl.
*A61K 38/51* (2006.01)
*A61K 38/19* (2006.01)
(Continued)

(52) U.S. Cl.
CPC ................. *A61K 38/51* (2013.01); *A61K 35/12* (2013.01); *A61K 38/19* (2013.01); *A61K 38/47* (2013.01); *C12Y 302/01035* (2013.01); *C12Y 402/02004* (2013.01)

(58) Field of Classification Search
None
See application file for complete search history.

(56) References Cited

U.S. PATENT DOCUMENTS

| 5,997,863 | A | * | 12/1999 | Zimmermann et al. ..... 424/94.5 |
| 2011/0008312 | A1 | | 1/2011 | Suzuki et al. |

FOREIGN PATENT DOCUMENTS

| JP | 4-330280 A | 11/1992 |
| JP | 10-265503 A | 10/1998 |
| JP | 11-147837 A | 6/1999 |

(Continued)

OTHER PUBLICATIONS

Bradbury et al., "Chondroitinase ABC promotes functional recovery after spinal cord injury," *Nature*, vol. 416, pp. 636-640 (Apr. 11, 2002).

(Continued)

*Primary Examiner* — Patricia A Leith
*Assistant Examiner* — Erin M Bowers
(74) *Attorney, Agent, or Firm* — Knobbe, Martens, Olson & Bear, LLP

(57) ABSTRACT

Provided is a skeletal muscle regeneration promoter for a muscular disorder or myopathy comprising a chondroitinase as an active component, which skeletal muscle regeneration promoter enhances, when administered into a muscular fiber of a mammal with the muscular disorder or myopathy, the regeneration of such a muscular fiber. The above-mentioned chondroitinase degrades chondroitin sulfate that is present at the outer perimeter of the above-mentioned muscular fiber; and thereby inhibition of the regeneration of the muscular fiber by the above-mentioned chondroitin sulfate disappears, which makes it possible to enhance the regeneration and enlargement of such a muscular fiber.

3 Claims, 4 Drawing Sheets

(51) Int. Cl.
*A61K 38/47* (2006.01)
*A61K 35/12* (2015.01)

(56) References Cited

FOREIGN PATENT DOCUMENTS

| WO | WO 2004/110359 A2 | 12/2004 |
| WO | WO 2009/072654 A1 | 11/2009 |
| WO | WO 2011/004911 A1 | 1/2011 |

OTHER PUBLICATIONS

Koyama et al., "Functional analysis of chondroitin sulfate in muscle differentiation," *Journal of Japanese Biochemical Society*, Shoroku CD, page ROMBUNNO. 3P-0090 (2010).

Laabs et al., "Chondroitin sulfate proteoglycans in neural development and regeneration," *Current Opinion in Neurobiology*, vol. 15, pp. 116-120 (2005).

Miura et al., "Decorin binds myostatin and modulates its activity to muscle cells," *Biochemical and Biophysical Research Communications*, vol. 340, pp. 675-680 (2006).

Silver et al., "Regeneration beyond the glial scar," *Nature Reviews, Neuroscience*, vol. 5, pp. 146-156 (Feb. 2004).

Villena et al., "Dermatan Sulfate Exerts an Enhanced Growth Factor Response on Skeletal Muscle Satellite Cell Proliferation and Migration," *Journal of Cellular Physiology*, vol. 198, pp. 169-178 (2004).

Yabuta et al., "Expression variation of chondroitin sulfate in skeletal muscle differentiation process entailing multinucleation," *Abstracts of Annual Meeting of the Pharmaceutical Society of Japan*, vol. 128th, No. 3, p. 48, 27PE-am122 (Mar. 5, 2008).

Extended European Search Report for European Patent Application No. 12832558.6, issued on Feb. 25, 2015.

Bertolotto et al., "Immunohistochemical Localization of Chondroitin Sulfate in Normal and Pathological Human Muscle," *Journal of the Neurological Sciences*, vol. 73(3), pp. 233-244 (1986).

Notification of Transmittal of Copies of Translation of the International Preliminary Report on Patentability and Written Opinion of the International Searching Authority for International Patent Application No. PCT/JP2012/073794, mailed on Mar. 27, 2014.

* cited by examiner

SKELETAL MUSCLE REGENERATION PROMOTER

CROSS-REFERENCE TO RELATED APPLICATIONS

This application is the U.S. National Phase under 35 U.S.C. §371 of International Application PCT/JP2012.073794, filed Sep. 18, 2012, which was published in a non-English language, which claims priority to JP Application No. 2011-202470, filed Sep. 15, 2011.

TECHNICAL FIELD

The present invention relates to a skeletal muscle regeneration promoter for muscular disorders or myopathies, and in particular relates to a skeletal muscle regeneration promoter capable of enhancing the regeneration of the muscular fiber in muscular disorder or myopathy without affecting healthy muscular fibers.

BACKGROUND ART

When muscles (muscular substances and muscular tissues) of healthy mammals including human are applied with an excessive burden, part of such muscles are worn out. Yet, such muscles normally have a capacity for regeneration and part of the above-mentioned worn muscles promptly regenerates and enlarges for bearing the above-mentioned burden.

The regeneration and enlargement of the above-mentioned muscle normally take place as follows: that is, when the above-mentioned muscle is given stimulation such as the above-mentioned burden, satellite cells, which are located between the basal membrane of cells of the muscular fiber of such a muscle (myocytes) and sarcolemma membrane are activated to begin proliferation. Here, the above-mentioned satellite cell corresponds to a stem cell that possesses ability to differentiate to multiple lineages of cells (pluripotency) and ability to maintain their pluripotency even after undergoing cell division (self-renewing ability). And, the above-mentioned proliferated satellite cells become myoblast cells, from which cells of the muscular fiber originate, and the resulting myoblast cells fuse with existing muscular fibers; and muscles containing such fused muscular fibers will regenerate and enlarge.

On the other hand, in a patient with the muscular disorder who for some reason has damage (disease) in the muscle, an ability of the above-mentioned muscle to regenerate is extremely decreased, or the above-mentioned muscular fiber is easily degraded (worn out) even if the ability of such a muscle to regenerate is maintained. Due to this, the rate of degradation of the above-mentioned muscle exceeds the rate of regeneration thereof in the above-mentioned patient with the muscular disorder, which often brings about muscular atrophy.

In addition, in a patient with muscular dystrophy among the above-mentioned muscular disorders, which is a typical myopathy, the rate of degradation of the above-mentioned muscular fiber is higher than the rate of regeneration thereof in relative to a healthy subject even though the degradation and regeneration of the above-mentioned muscular fiber repeatedly take place. Due to this, the above-mentioned patient with the myopathy will have a gradually progressing atrophy of his/her own muscles, which results in death early in life.

As a method of treating the muscular disorder or myopathy stated above, a number of methods of enhancing (improving) the rate of regeneration of the above-mentioned muscle have been reported (Non-patent Documents 1 to 3). Yet, as it stands at this point in time, a good method of treatment has not been established.

Meanwhile, in nerve regenerative medicine, examples of methods of regenerating (elongating) damaged axons include a method of degrading chondroitin sulfate (CS) present outside cells in the nervous system.

The above-mentioned chondroitin sulfate (CS) is a major extracellular matrix component in the nervous system and is a component involved in formation of the neural network. Meanwhile, the above-mentioned chondroitin sulfate (CS) serves as a component that inhibits the regeneration of the above-mentioned axon in the cranial nerve system of an adult who has had a traumatic injury such as a spinal cord injury. That is, the above-mentioned chondroitin sulfate (CS) serves both as a necessary component and an inhibitory component in accordance with the situation.

In view of this, when a chondroitinase of bacterial origin including for example chondroitinase ABC (ChABC) is administered to an area of nerve damage affected by the above-mentioned traumatic injury, wherein the chondroitinase degrades chondroitin sulfate (CS) that is expressed in such an area, such a chondroitinase ABC exerts its action on the above-mentioned chondroitin sulfate (CS) to degrade (remove) such a chondroitin sulfate (CS). Then, the component inhibiting the regeneration of axon in the above-mentioned nervous system disappear and therefore the regeneration of such an axon is promoted not only to construct a new neural network but also to achieve the recovery of neural functions. A number of examples like this have been reported (Non-patent Documents 4 to 6).

In addition, examples of diseases associated with nerve compression disorders in the above-mentioned nervous system include intervertebral disc hernia. The above-mentioned intervertebral disc hernia is a disease caused by bulging out of the nucleus pulposus in the intervertebral disc or the like, in which symptoms including lower back pain or the like develop because the bulged nucleus pulposus irritates the nerves around the nucleus pulposus.

As for a treatment of the above-mentioned intervertebral disc hernia, Japanese Patent Application Laid-Open Publication No.11-147837 (Patent Document 1) discloses a pharmaceutical composition for administration into spinal epidural space that contains a glycosaminoglycan-degrading enzyme and a pharmaceutical carrier. The above-mentioned glycosaminoglycan-degrading enzyme is an enzyme that degrades glycosaminoglycan into unsaturated oligosaccharides and unsaturated disaccharides and corresponds to a chondroitinase which degrades chondroitin sulfate (CS). Here, by administering the pharmaceutical composition containing the above-mentioned chondroitinase into spinal epidural space, the nucleus pulposus in the herniated intervertebral disc that migrates to such a spinal epidural space is efficiently digested and the phagocytosis of the nucleus pulposus by inflammatory cells is promoted. As a result, the above-mentioned Patent Document 1 describes that the invention thereof diminishes the nucleus pulposus migrated into the epidural space in an extremely efficient and effective fashion; and, on the top of that, there is an effect that the spinal cord is not affected at all.

In addition, there are examples where the above-mentioned chondroitinase is applied in a treatment of hypertrophic scar or keloid. For instance, WO 2009/072654 (Patent Document 2) discloses a promoter of elastic fiber formation that contains an enzyme degrading chondroitin sulfate A, chondroitin sulfate B, and chondroitin sulfate C. It is described therein that the administration of the above-mentioned promoter of elastic fiber formation to the area of the above-mentioned hypertrophic scar or keloid enables evaluation of the process of tissue normalization, which leads to reduction in the tissue volume of such a hypertrophic scar or keloid and complete cure of such a keloid or the like.

By way of example of enzymes degrading CS, there are chondroitinases such as ChABC, chondroitinase AC, chondroitinase ACII, chondroitinase ACIII, chondroitinase B, chondroitinase C, chondroitin sulfate ABC exolyase, and the like. In recent years, it has been known that hyaluronic acid-degrading enzymes of mammalian origin including Hyal-1 and PH-20 have an activity of degrading CS as well (Non-patent Documents 7 and 8).

PRIOR ART DOCUMENTS

Non-Patent Documents

Non-patent Document 1: Ikuya Nonaka, "Rinsho Shinkeigaku 12", 1998, p. 997-1000
Non-patent Document 2: Grounds, M. D., "Curr. Opin. Neurol. 12", 1999, p. 535-543
Non-patent Document 3: Anderson, J. E., "Biochem. Cell Biol. 76", 1998, p. 13-26
Non-patent Document 4: Bradbury, E. J., and seven others, "Nature 416", 2002, p. 636-640
Non-patent Document 5: Silver, J., and the other, "Net. Rev. Neurosci. 5", 2004, p. 146-156
Non-patent Document 6: Carulli, D., and three others, "Curr. Opin. Neurobiol. 15", 2005, p. 116-120
Non-patent Document 7: Robert, S and Mark J. J., "Chem. Rev. 106", 2006, p. 818-839
Non-patent Document 8: Hafida, E. H., "Arthritis Res Ther 7", 2005, p. R756-R768

Patent Documents

Patent Document 1: Japanese Patent Application Laid-Open Publication No.11-147837
Patent Document 2: WO 2009/072654

SUMMARY OF THE INVENTION

However, there is no description of treatment of the muscular disorders or myopathies stated above in the above-mentioned Non-patent Documents 1 to 6 and the above-mentioned Patent Documents 1 and 2; and no methods of treating those are not established at this point in time, which is problematic.

Meanwhile, it has been found out by the present inventors that, in an in vitro culture system of myoblast cells (C2C12 cells), the progression of muscle differentiation is promoted by lowering the expression level of chondroitin sulfate (CS). In view of this, enhanced differentiation of the muscle, enlargement of the muscular fiber, and induced regeneration of the muscle may be expected also in vivo by lowering the expression amount of the above-mentioned chondroitin sulfate (CS).

In view of this, the present invention is made for the purpose of solving the above-mentioned problem and relates to a skeletal muscle regeneration promoter for muscular disorders or myopathies. To be specific, an object thereof is to provide a skeletal muscle regeneration promoter capable of enhancing the regeneration of the muscular fiber in muscular disorder or myopathy without affecting healthy muscular fibers.

The present inventor intensively studied to complete a novel skeletal muscle regeneration promoter according to the present invention as a skeletal muscle regeneration promoter (skeletal muscle regeneration therapeutic agent) for muscular disorders or myopathies.

That is, the skeletal muscle regeneration promoter according to the present invention is a skeletal muscle regeneration promoter that contains an enzyme degrading chondroitin sulfate as an active component and, when administered to the muscular fiber of mammals with muscular disorders or myopathies, enhances the regeneration of such a muscular fiber.

Another aspect of the present invention relates to an enzyme degrading chondroitin sulfate which is used for the purpose of enhancing the regeneration of the skeletal muscle in muscular disorder or myopathy, which enzyme enhances the regeneration of such a muscular fiber when administered to the muscular fiber of the mammal with the muscular disorder or myopathy.

Still another aspect of the present invention relates to a method of promoting the regeneration of the skeletal muscle in muscular disorder or myopathy, which method comprises the step of administering an amount of the enzyme degrading chondroitin sulfate to the muscular fiber of the mammal with the muscular disorder or myopathy, which amount is effective for regeneration of the skeletal muscle.

Thereby, upon the administration of the skeletal muscle regeneration promoter containing the above-mentioned enzyme to the muscular fiber in the above-mentioned muscular disorder or the above-mentioned myopathy, such an enzyme will degrade chondroitin sulfate (CS) that is present at the outer periphery of the above-mentioned muscular fiber (cell). This degradation reduces the inhibition of regeneration in the muscular fiber by the above-mentioned chondroitin sulfate (CS), which makes it possible to enhance the regeneration and enlargement of such a muscular fiber. Further, the above-mentioned enzyme barely exhibits adverse effects on healthy muscular fibers that are not affected by either the above-mentioned muscular disorder or the above-mentioned myopathy and is highly safe. Due to this, the skeletal muscle regeneration promoter of the present invention is effective as a skeletal muscle regeneration promoter that restricts its target to the muscular fiber in the above-mentioned muscular disorder or the above-mentioned myopathy and is excellent in safety.

Further, the present invention can be composed such that the above-mentioned enzyme contains any of chondroitinase ABC, chondroitinase AC, chondroitinase ACII, chondroitinase ACIII, chondroitinase B, chondroitinase C, chondroitin sulfate ABC exolyase, and a hyaluronic acid-degrading enzyme of mammalian origin that has an activity of degrading chondroitin sulfate.

Further, the present invention can be composed such that the above-mentioned myopathy include any of congenital or progressive muscular dystrophy, congenital or distal myopathy, myotonic dystrophy, myotonia syndrome, mitochondrial diseases, periodic paralysis, malignant hyperpyrexia, and ion channel diseases.

Further, the present invention can be composed such that the above-mentioned skeletal muscle regeneration promoter is an injectable formulation with the above-mentioned enzyme as an active component.

Further, the present invention can be composed such that the dosage amount of the above-mentioned enzyme is 0.1 mIU/g to 10.0 mIU/g per dose.

Further, the present invention can be composed such that the administration mode of the above-mentioned enzyme is a mode in which the enzyme of a predetermined concentration ranging from 0.5 IU/mL to 200.0 IU/mL is administered to plural sites throughout a predetermined area of the above-mentioned muscular fiber at an each dosage amount ranging from 1 μL to 5000 μL.

Further, the present invention can be composed such that the above-mentioned skeletal muscle regeneration promoter is used in combination with a treatment comprising any of a stem cell therapy and a therapy using an inhibitor of myostatin which is derived from cytokines having a function of suppressing muscle mass.

Further, according to the present invention, also provided is a therapeutic agent for muscular disorders or myopathies with an enzyme degrading chondroitin sulfate as an active component.

Another aspect of the present invention relates to an enzyme degrading chondroitin sulfate that is used for the purpose of treating muscular disorders or myopathies.

Still another aspect of the present invention relates to a method of treating muscular disorders or myopathies, the method comprising the step of administering an amount of an enzyme degrading chondroitin sulfate to mammals with the muscular disorder or myopathy, which amount is effective for treating the muscular disorder or myopathy.

To be more specific, the present invention is as follows:

(1) A skeletal muscle regeneration promoter for a muscular disorder or myopathy comprising an enzyme degrading chondroitin sulfate as an active component, which skeletal muscle regeneration promoter enhances, when administered into a muscular fiber of a mammal with the muscular disorder or myopathy, the regeneration of the muscular fiber.

(2) The skeletal muscle regeneration promoter according to (1), wherein the above-mentioned enzyme comprises any of chondroitinase ABC, chondroitinase AC, chondroitinase ACII, chondroitinase ACIII, chondroitinase B, chondroitinase C, chondroitin sulfate ABC exolyase, and a hyaluronic acid-degrading enzyme of mammalian origin having an activity of degrading the above-mentioned chondroitin sulfate.

(3) The skeletal muscle regeneration promoter according to (1) or (2), wherein the above-mentioned myopathy comprises any of congenital or progressive muscular dystrophy, congenital or distal myopathy, myotonic dystrophy, myotonia syndrome, a mitochondrial disease, periodic paralysis, malignant hyperpyrexia, and an ion channel disease.

(4) The skeletal muscle regeneration promoter according to any one of (1) to (3), wherein the above-mentioned skeletal muscle regeneration promoter is an injectable formulation with the above-mentioned enzyme as an active component.

(5) The skeletal muscle regeneration promoter according to any one of (1) to (4), wherein the dosage amount of the above-mentioned enzyme is 0.1 mIU/g to 10.0 mIU/g per dose.

(6) The skeletal muscle regeneration promoter according to any one of (1) to (5), wherein the administration mode of the above-mentioned enzyme is a mode in which the enzyme of a predetermined concentration ranging from 0.5 IU/mL to 200.0 IU/mL is administered to plural sites throughout a predetermined area of the above-mentioned muscular fiber at an each dosage amount ranging from 1 μL to 5000 μL.

(7) The skeletal muscle regeneration promoter according to any one of (1) to (6), wherein the above-mentioned skeletal muscle regeneration promoter is used in combination with a treatment comprising any of a stem cell therapy and a therapy using an inhibitor of myostatin derived from a cytokine having a function of suppressing muscle mass.

(8) A therapeutic agent for the muscular disorder or myopathy with an enzyme degrading chondroitin sulfate as an active component.

EFFECT OF THE INVENTION

With the skeletal muscle regeneration promoter for the muscular disorder or myopathy according to the present invention, it becomes possible to enhance the regeneration of the muscular fiber in the muscular disorder or myopathy without affecting healthy muscular fibers. In addition, the present invention can be used as a skeletal muscle promoting reagent.

DESCRIPTION OF THE EMBODIMENTS

Figure 1:
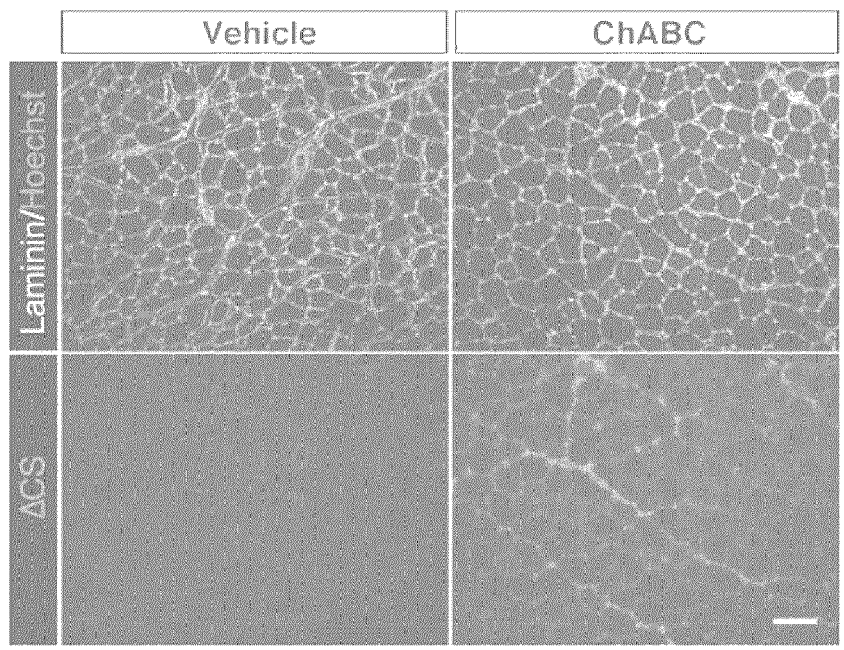
FIG. 1 is a figure showing one example of the ΔCS observation and Laminin/Hoechst observation of the muscular fiber of a healthy mouse at seven days after the administration of saline (vehicle); and a figure showing one example of the ΔCS observation and Laminin/Hoechst observation of the muscular fiber of a healthy mouse at seven days after the administration of chondroitinase ABC (ChABC) (photographs).

Embodiments of the skeletal muscle regeneration promoter according to the present invention will be described below with reference to the accompanying drawings to facilitate understanding of the present invention. It is to be noted that the following embodiment is one example embodying the present invention and is not of the nature to limit the technical scope of the present invention.

<Skeletal Muscle Regeneration Promoter>

The skeletal muscle regeneration promoter according to the present invention is a skeletal muscle regeneration promoter for muscular disorders or myopathies. Further, the skeletal muscle regeneration promoter according to the present invention is a skeletal muscle regeneration promoter that contains an enzyme degrading chondroitin sulfate (CS) as an active component and, when administered to the muscular fiber of mammals with the muscular disorder or myopathy, enhances the regeneration of such a muscular fiber.

Here, the enzyme that is contained as an active component is not particularly restricted as long as it is an enzyme that degrades chondroitin sulfate (CS) present on the periphery of the muscular fiber (cell). As the above-mentioned enzyme, for example, chondroitinases including chondroitinase ABC (ChABC), chondroitinase AC, chondroitinase ACII, chondroitinase ACIII, chondroitinase B, chondroitinase C, and chondroitin sulfate ABC exolyase can be used. Further, an enzyme having an activity of degrading chondroitin sulfate (CS) may be used as well. For instance, a hyaluronic acid-degrading enzyme of mammalian origin such as HYAL-1 or PH-20 can be used (Non-patent Documents 7 and 8).

Here, chondroitinase ABC is, for example, derived from *Proteus vulgaris;* and chondroitinase AC is, for example, derived from *Flavobacterium heparinum.* Further, chondroitinase ACII is, for example, derived from *Arthrobacter aurescens;* and chondroitinase ACIII is, for example, derived from *Flavobacterium* sp. Hp102. Further, chondroitinase B is, for example, derived from *Flavobacterium heparinum;* and chondroitinase C is, for example, derived from *Flavobacterium* sp. Hp102.

Further, the above-mentioned enzyme may be one kind of enzyme or may be a mixture of plural kinds of enzymes. Further, the enzyme described in the present specification encompasses both of these meanings.

Further, from the viewpoint of the enhancement of degradation of chondroitin sulfate (CS), it is preferred that the above-mentioned enzyme be ChABC or a hyaluronic acid-degrading enzyme of mammalian origin. In the case of such a ChABC, it is further preferred to be ChABC derived from *Proteus vulgaris*.

Further, the skeletal muscle regeneration promoter containing the above-mentioned enzyme can be prepared and formulated by a known method in pharmaceutics. Here, the above-mentioned skeletal muscle regeneration promoter may be in any state such as a solution state, frozen state, or dried state.

Further, the skeletal muscle regeneration promoter containing the above-mentioned enzyme is used mainly in an injectable formulation. Here, in cases where the above-mentioned skeletal muscle regeneration promoter is used in an injectable formulation in a solution state, such an injectable formulation can be filled and sealed in a container such as an ampule, vial, or syringe for injection; distributed as it is or stored; and used in the administration as an injection solution. Further, in cases where the above-mentioned skeletal muscle regeneration promoter is used in an injectable formulation in a dried state, such an injectable formulation is kept in the above-mentioned container in a sealed state; distributed or stored; dissolved in a solvent (solvent medium) such as distilled water for injection, (phosphate buffered) saline, aqueous glucose solution, or aqueous sorbitol solution before the administration; and used in the administration as an injection solution.

Further, the above-mentioned muscular disorder is not particularly restricted as long as it is a non-hereditary disease in which muscles of mammals are damaged. Examples of the above-mentioned muscular disorder include connective tissue diseases such as dermatomyositis, polymyositis, polyarteritis nodosa, polymyalgia rheumatica, SLE (systemic lupus erythematosus), rheumatoid arthritis, Sjogren's syndrome, systemic scleroderma, or mixed connective tissue disease; inflammatory myopathies including infectious diseases such as toxoplasmosis, trichomoniasis, myositis purulenta, gas gangrene, necrotizing myositis, or acute viral myositis; endocrine myopathies such as hypothyroidism or hyperthyroidism; and toxic myopathies induced by a therapeutic agent for hyperlipidemia or steroid and the like. Further, even though the above-mentioned muscular disorder is different from a myopathy in which the muscle becomes atrophic with the cause in the muscle per se, a neuropathy with the cause in the nerve is also relevant, wherein the muscle becomes atrophic because of damages in anterior horn cells in the spinal cord and the peripheral nerve. Thus, examples of such a muscular disorder may include infantile spinal muscular atrophy (Werdnig-Hoffmann disease), Charcot-Marie-Tooth disease, hypomyelinogenesis congenita, and amyotrophic lateral sclerosis.

Further, the above-mentioned myopathy is not particularly restricted as long as it is a hereditary disease in which muscles of mammals are damaged. Examples of the above-mentioned myopathy include congenital or progressive muscular dystrophy; congenital and distal myopathy; myotonia syndromes including myotonic dystrophy; mitochondrial diseases; and ion channel diseases including periodic paralysis and malignant hyperpyrexia. Further, examples of the above-mentioned muscular dystrophy include Duchenne muscular dystrophy and Becker muscular dystrophy.

Further, it is preferred that the above-mentioned myopathy be muscular dystrophies from the viewpoint of the enhancement of the regeneration of the muscular fiber by degradation of chondroitin sulfate (CS). Of such muscular dystrophies, it is further preferred to be Duchenne muscular dystrophy.

Further, the above-mentioned mammal is not particularly restricted as long as it is a mammal having the muscular fiber (cell) in muscular disorders or myopathies. Examples of the above-mentioned mammal include humans, chimpanzees, dogs, rats, and mice.

Further, a method of administering the skeletal muscle regeneration promoter containing the above-mentioned chondroitinase to the muscular fiber of the mammal with the above-mentioned muscular disorder or the above-mentioned myopathy is not particularly restricted as long as it is a method of infiltrating the above-mentioned skeletal muscle regeneration promoter into the cell periphery of the above-mentioned muscular fiber. Examples of the above-mentioned method of administration include subcutaneous administration, intravenous administration, intra-arterial administration, intramuscular administration, intrarectal administration, and percutaneous administration and intramuscular administration is preferred.

Further, the dosage amount of the above-mentioned enzyme is not particularly restricted as long as it is a dosage amount at which regeneration of the above-mentioned muscular fiber is enhanced. From the viewpoint of the enhancement of the regeneration of the muscular fiber by degradation of the above-mentioned chondroitin sulfate (CS), it is preferred that a dosage amount of the above-mentioned enzyme be, for example, 0.1 mIU/g to 10.0 mIU/g per dose. If a human with a body weight of 60 kg is considered as a subject, examples of the dosage amount of the above-mentioned enzyme include a range from 0.1 mIU/g to 6.7 mIU/g.

Further, the administration mode of the above-mentioned enzyme is not particularly restricted as long as it is an administration mode whereby the regeneration of the above-mentioned muscular fiber is enhanced. From the viewpoint of the enhancement of the regeneration of the muscular fiber by the degradation of the above-mentioned chondroitin sulfate (CS), it is preferred that the administration mode of the above-mentioned enzyme be, for example, a mode in which an enzyme of a predetermined concentration ranging from 0.5 IU/mL to 200.0 IU/mL is administered to plural sites over a predetermined area of the above-mentioned muscular fiber at an each dosage amount ranging from 1 µL to 5000 µL, which makes it possible to exhaustively degrade chondroitin sulfate (CS) that is expressed in the predetermined area of the above-mentioned muscular fiber. For instance, in cases where the above-mentioned enzyme is ChABC, the administration of 2.0 IU/mL of ChABC to plural sites (for example, two sites to 10 sites) over the predetermined area of the above-mentioned muscular fiber at an each dosage amount of 30 µL makes it possible to effectively regenerate the above-mentioned muscular fiber and enhance the enlargement thereof. If a human with a body weight of 60 kg is considered as a subject, examples of the common dosage amount for intramuscular administration include a range from 1000 µL to 2000 µL.

Here, 1 U (unit) of the enzyme in the present specification is defined as the amount of the enzyme at which 1 micromole of reaction product is released from such an enzyme for 1 minute under a condition in the proximity of optimum pH and optimum temperature. For instance, 1 U of the above-mentioned ChABC is defined as an amount of the enzyme at which 1 micromole of unsaturated disaccharide is released from chondroitin 6-sulfate at pH8.0 and 37° C. for 1 minute. The same is applied in a different type of chondroitinase.

Further, the above-mentioned enzyme is preferably an enzyme that is purified to the extent that it can be used as a skeletal muscle regeneration promoter (medicine, therapeutic agent), which enzyme does not substantially contain substances which are unacceptable to be contained as the skeletal muscle regeneration promoter. Further, the above-mentioned enzyme preferably has a specific activity equal to or more than a predetermined one. For instance, in cases where the above-mentioned enzyme is the above-mentioned ChABC, it is preferred to be an enzyme purified to a specific activity of 100 U/mg protein or higher. Further, it is more preferred to be an enzyme purified to a specific activity of 300 U/mg protein or higher.

Further, as long as the skeletal muscle regeneration promoter according to the present invention contains the above-mentioned enzyme as an active component, it may as well contain additives that are usually used in the skeletal muscle regeneration promoter (pharmaceutical), which additives include commonly-used excipients, binders, lubricants, coloring agents, disintegrants, buffering agents, isotonic agents, preservatives, and soothing agents.

For instance, in cases where the skeletal muscle regeneration promoter according to the present invention is used as an injectable formulation, a solution in which the above-mentioned enzyme is dissolved in a solvent such as distilled water for injection, (phosphate buffered) saline, aqueous glucose solution, or aqueous sorbitol solution only to a predetermined concentration is prepared; and the prepared solution mentioned above is only to use as an injectable formulation.

EXAMPLES

As the examples of the present invention, evaluation methods and test examples using mice will be concretely described below. However, the application of the present invention is by no means limited to the Examples.
<Evaluation Method>
(1-1) Preparation of Section of Muscular fiber A slice of the (skeletal) muscular fiber of a mouse that is subjected to the evaluation of the regeneration of the muscular fiber is extracted by cutting the muscular fiber of the anterior tibialis muscle of such a mouse at right angle to such a muscular fiber. The way to cut muscle fibers allows an extracted slice to have a cross-section, which is arranged perpendicular to the long axis of a muscle fiber and resulted in a cross-section in a lateral direction. The above-described slice is placed into isopentane pre-cooled with liquid nitrogen and rapidly frozen to prevent the muscle fiber from degrading.

Next, the above-mentioned rapidly-frozen slice is prepared into sections with a thickness of 10 µm using a cryostat, applied onto an APS (aminosilane)-coated glass slide (manufactured by Matsunami Glass Ind., Ltd.) on a paraffin stretching table, dried and then stored at −80° C. Thereby, a section for evaluation can be obtained.
(1-2) Observation of Morphology of Muscular fiber (Cell) by Immunofluorescence Staining The section prepared in the above-mentioned (1-1) is treated for 30 minutes using paraformaldehyde (PFA) with a concentration of 4% (w/v) in a solvent of phosphate buffered physiological saline (PBS, pH7.4) for fixation.

Next, the above-mentioned fixed section is washed with the above-mentioned PBS, treated with an M.O.M. mouse Ig blocking reagent (M.O.M., a reagent of Immunodetection kit, manufactured by Vector Laboratories, United Kingdom) containing 2% goat serum, and left to stand for one hour for carrying out a blocking treatment.

Meanwhile, either an anti-laminin antibody (manufactured by Sigma) or anti-CS stub antibody (2-B-6) (manufactured by Seikagaku Corporation) is diluted with and mixed in an M.O.M. dilution solution (a reagent of M.O.M. Immunodetection kit, manufactured by Vector) to prepare a mixed solution as a primary antibody. The above-mentioned anti-laminin antibody is diluted 400 folds by volume to the above-mentioned M.O.M. dilution solution while the above-mentioned anti-CS stub antibody is diluted 200 folds by volume to the above-mentioned M.O.M. dilution solution.

Here, the above-mentioned anti-laminin antibody is an antibody that recognizes laminins which are present on the basal lamina of muscular fibers (cells). Use thereof in conjunction of a secondary antibody [Alexa Fluor 488 goat anti-rabbit IgG (H+L) (manufactured by Invitrogen)] that recognizes the above-mentioned anti-laminin antibody enables the periphery of such muscular fibers to be observed as green color fluorescence. Further, the above-mentioned anti-CS stub antibody is an antibody that recognizes the stub structure of chondroitin sulfate (CS), the structure being generated by degrading chondroitin sulfate (CS) by the above-mentioned enzyme degrading chondroitin sulfate. Use thereof in conjunction of a secondary antibody [Alexa Fluor 594 goat anti-mouse IgG1 (gamma 1) (manufactured by Invitrogen)] that recognizes the above-mentioned anti-CS stub antibody enables the stub structure of chondroitin sulfate (CS) in the muscular tissue section to be detected as a red color fluorescence.

The above-mentioned prepared primary antibody is placed dropwise to the section after the above-mentioned blocking treatment and allowed to react at 4° C. overnight; and the section after such a reaction is washed with the above-mentioned PBS three times.

Meanwhile, Alexa Fluor 488 goat anti-rabbit IgG (H+L) (manufactured by Invitrogen) and Alexa Fluor 594 goat anti-mouse IgG1 (gamma 1) (manufactured by Invitrogen) are diluted with and mixed in the above-mentioned M.O.M. dilution solution to prepare a mixed solution as a secondary antibody. The above-mentioned Alexa Fluor 488 goat anti-rabbit IgG (H+L) is diluted 200 folds by volume to the above-mentioned M.O.M. dilution solution while the above-mentioned Alexa Fluor 594 goat anti-mouse IgG1 (gamma 1) is diluted 200 folds by volume to the above-mentioned M.O.M. dilution solution.

And, the above-mentioned prepared secondary antibody is placed dropwise to the section after the above-mentioned washing and allowed to react at 37° C. for 1 hour; and the section after such a reaction is washed with the above-mentioned PBS three times. Further, to the section after such a washing, Hoechst 33342 (manufactured by Invitrogen) diluted with the above-mentioned PBS is placed dropwise and allowed to react at room temperature for 20 minutes. Here, the above-mentioned Hoechst 33342 is diluted 500 folds by volume to the above-mentioned PBS. The above-mentioned Hoechst 33342 stains the central nucleus of the muscular fiber in a fluorescent blue color, thereby enabling observation of such a central nucleus of the muscular fiber.

Further, the above-mentioned section after the reaction is washed as appropriate with the above-mentioned PBS; and then the section after such a washing is mounted using a prescribed mounting agent (FLUOROSHIELD, manufactured by ImmunoBioScience Corp.), followed by observation by a specified All-in-one fluorescence microscope (BZ-800, manufactured by KEYENCE). In order to clarify the presence (localization) of the nucleus in the muscular fiber, the setting condition of the above-mentioned All-in-one fluorescence microscope is set to a setting condition where the fluorescent blue color in digitalized picture images is altered to a pseudo color of red color.

(1-3) Imaging Analysis

Quantitative evaluation is carried out for the muscular fiber by analyzing picture images of the muscular fiber obtained the above-mentioned (1-2). In the case of carrying out the above-mentioned quantitative evaluation, the following two kinds of values are calculated to thereby carry out the evaluation.

(1-3-1) Cross-Sectional Area of Cell of Muscular Fiber

In the above-mentioned picture image, all of the muscular fibers having the central nucleus that were present in one visual field (918 μm×634 μm) (100 to 200 fibers/visual field, at least three visual fields per sample) were extracted and the cross-sectional area (CSA) of all of the cells of such an extracted muscular fiber was measured. And, a mean cross-sectional area per cell was calculated by dividing the above-mentioned measured cross-sectional area by the number of the extraction. Here, a larger mean cross-sectional area per cell indicates that the regeneration (proliferation) and enlargement of the above-mentioned muscular fiber is more enhanced (activated).

(1-3-2) Proportion of Cells of Muscular Fiber in which Central Nucleus is Not Present In the above-mentioned picture images, all of the muscular fibers that were present in one visual field (918 μm×634 μm) (100 to 200 fibers/visual field, at least three visual fields per sample) were extracted; and among the cells of such an extracted muscular fiber, the number of cells of muscular fiber in which the central nucleus was not present was measured. And, a proportion (%: percentage) was calculated by dividing the above-mentioned measured number of cells of the muscular fiber in which the central nucleus was not present by the number of the extraction. A higher proportion of the above-mentioned cells in which the central nucleus is not present indicates that the regeneration and enlargement of the above-mentioned muscular fiber as well as the stabilization of the muscular fiber is more enhanced.

<Test Example>

(2-1) Pharmacological Test for Pharmacological Effects Using Healthy (Normal) Mice Whether or not the administration of the skeletal muscle regeneration promoter according to the present invention to the muscle (fiber) of a healthy mouse enhanced a regeneration process of such a muscular fiber was examined.

Here, as the skeletal muscle regeneration promoter according to the present invention, an injectable formulation obtained by aseptically dissolving chondroitinase ABC (EC4.2.2.4, manufactured by Seikagaku Corporation) (ChABC) in saline (manufactured by Otsuka Pharmaceutical Co., Ltd.) at a predetermined concentration (for example, 2.0 IU/mL) was used, which chondroitinase ABC is an enzyme that degraded the above-mentioned chondroitin sulfate (CS).

A wild type mouse (C57BL/10 lineage, equivalent to about 20 g, manufactured by Japan SLC, Inc.) at five weeks (age in weeks) to six weeks after birth was intraperitoneally administered with Somnopentyl (manufactured by Kyoritsu Seiyaku Corporation) and anesthetized. And then 30 μL of the above-mentioned injectable formulation was administered into the anterior tibialis muscle of the left hind limb of the above-mentioned wild type mouse using a prescribed syringe. The dosage amount of such an injectable formulation is thus a dosage amount equivalent to 60 mIU per dose in terms of the above-mentioned ChABC. For the above-mentioned mouse, the dosage amount of the above-mentioned ChABC turns out to be 3.0 mIU/g.

Further, as a control experiment, 30 μL of saline was solely administered into the anterior tibialis muscle of the right hind limb of the above-mentioned wild type mouse, which saline was one used for the above-mentioned injectable formulation.

Next, using a mouse at seven days immediately after the administration of each formulation (pharmacological agent), a section of muscular fiber was prepared by the above-mentioned (1-1) to (1-2) and the fluorescence observation was carried out.

Here, as for the above-mentioned fluorescence observation, employed were the ΔCS observation in which a fluorescence signal of the stub structure by the degradation of the above-mentioned chondroitin sulfate (CS) was solely observed and the Laminin/Hoechst observation in which the morphology of cells of an individual muscular fiber and the localization of the nucleus thereof were detected.

FIG. 1 is a figure showing one example of the ΔCS observation and Laminin/Hoechst observation of the muscular fiber of the healthy mouse at seven days after the administration of saline (vehicle); and a figure showing one example of the ΔCS observation and Laminin/Hoechst observation of the muscular fiber of the healthy mouse at seven days after the administration of ChABC. Note that the scale bar of white horizontal line at the lower left represents 100 μm.

In the ΔCS observation of the muscular fiber of the healthy mouse at seven days after the administration of the above-mentioned saline, as shown in FIG. 1, a fluorescence signal corresponding to the above-mentioned stub structure was not observed at all. It is thereby understood that the degradation of the above-mentioned chondroitin sulfate (CS) does not take place by the administration of the above-mentioned saline.

On the other hand, in the ΔCS observation of the muscular fiber of the healthy mouse at seven days after the administration of the above-mentioned ChABC, as shown in FIG. 1, it was observed that the outer perimeter of each of the muscular fibers was edged with the above-mentioned fluorescence signal. It is thereby understood that the degradation of the above-mentioned chondroitin sulfate (CS) takes place by the administration of the above-mentioned ChABC, the chondroitin sulfate being present at the periphery of the membrane of the above-mentioned muscular fiber.

Further, in the Laminin/Hoechst observation of the muscular fiber of the healthy mouse at seven days after the administration of the above-mentioned ChABC, as shown in FIG. 1, a fluorescence signal of red color indicating the central nucleus of the muscular fiber was not observed at all. Here, in cases where the muscular fiber having the above-mentioned central nucleus is present, it is implied that satellite cells involved in the regeneration and proliferation of the muscular fiber are activated. Due to this, a fact that no cells of the muscular fiber having the above-mentioned central nucleus are observed at all means that the above-mentioned satellite cells are not activated and the regeneration and enlargement of the muscular fiber are not in particular promoted by the administration of the above-mentioned saline and the above-mentioned ChABC. Therefore, it is thereby understood that the administration of the above-mentioned ChABC leads to the degradation of chondroitin sulfate (CS) in the muscular tissue but barely affects the regeneration and enlargement of the muscular fiber of the healthy mouse. In other words, it is suggested that the administration of the above-mentioned ChABC barely gives rise to adverse effects on healthy fibers and is highly safe.

(2-2) Pharmacological Test for Pharmacological Effects Using Mice with Muscular Disorder Next, whether or not the administration of the skeletal muscle regeneration promoter according to the present invention to the muscle of a mouse with a muscular disorder (damage) enhanced a regeneration process of such a muscular fiber was examined.

For the purpose of bringing on the above-mentioned muscular disorder in the muscle of the mouse, the following method was employed. That is, cardiotoxin (CTX) derived from *Naja mossambica mossambica*, which is also known as cobra venom, has the characteristics of, when administered to the muscle, destroying the plasma membrane of the muscular fiber of such a muscle to make such a muscular fiber undergo necrosis. Meanwhile, the above-mentioned CTX has a characteristic of not affecting (damaging) any of cells involved in the regeneration of the above-mentioned muscle, for example, satellite cells, the blood vessels, and the peripheral nerve. Due to this, even if the above-mentioned CTX is administered to the above-mentioned muscle, the regeneration of such a muscular fiber will sooner or later begin. Further, the necrosis of the muscular fiber begins immediately after the administration of the above-mentioned CTX; and when 24 hours (one day) immediately after such an administration pass, macrophages invade into the inside of the above-mentioned necrotic muscular fiber. And, when 72 hours (three days) immediately after the above-mentioned administration pass, muscle stem cells which indicate the regeneration of the muscular fiber begin to appear. That is to say, the administration of the above-mentioned CTX to the muscle is able to artificially give rise to diseases (damages) in the muscular fiber of such a muscle (See, for example, Jin, Y., and five others, "Acta Neuropathol. 99", 2000, p. 619-627).

In view of this, using a mouse whose (skeletal) muscle was administered with the above-mentioned CTX as a mouse model of a muscle damage (disease), whether or not further administration of the above-mentioned ChABC to such a mouse model of the muscle damage enhanced a regeneration process of such a muscle of such a mouse model of the muscle damage was examined.

First, only 30 μL of the above-mentioned CTX at a prescribed concentration (for example, 10 μM) was solely administered to the anterior tibialis muscle of the left hind limb of the above-mentioned wild type mouse; and the mouse was designated as a first mouse. Note that the above-mentioned CTX was prepared using saline as an injectable formulation with the above-mentioned concentration and administered by a syringe.

Next, a different wild type mouse from the above-mentioned first mouse was provided; and only 30 μL of CTX with the above-mentioned concentration was solely administered to the anterior tibialis muscle of the left hind limb of such a wild type mouse. When three days immediately after such administration passed, only 30 μL of ChABC with the above-mentioned predetermined concentration (2.0 IU/mL) was additionally administered to such an anterior tibialis muscle; and that mouse was designated as a second mouse. Here, the dosage amount of the above-mentioned ChABC is 60 mIU per dose.

Note that the reason why, in the above-mentioned second mouse, the above-mentioned ChABC was administered when three days immediately after the administration of the above-mentioned CTX passed is because fusion of myoblast cells derived from the above-mentioned satellite cells was observed when such three days passed; and therefore the inventors thought that, with the degradation of the above-mentioned chondroitin sulfate (CS) expressed at that period of time, the regeneration and enlargement of the above-mentioned muscular fiber were significantly enhanced.

Further, a different wild type mouse from the above-mentioned first mouse and the above-mentioned second mouse is provided; and 30 μL of mixed solution of CTX and ChABC (in a mixed solution, CTX concentration: 10 μM, ChABC concentration: 2.0 IU/mL) was administered to the anterior tibialis muscle of the left hind limb of such a wild type mouse; and that mouse is designated as a third mouse. Here, the amount of the above-mentioned ChABC mixed is equivalent to the above-stated dosage amount, which is 60 mIU.

And then, using a mouse at seven days immediately after the administration of each formulation, a section of the muscular fiber was prepared by the above-mentioned (1-1) to (1-3); and the fluorescence observation and imaging analysis were carried out.

Here, the above-mentioned Laminin/Hoechst observation was employed for the above-mentioned fluorescence observation; and the above-mentioned imaging analysis was used for the cross-sectional area of the cell of the muscular fiber.

Figure 2:
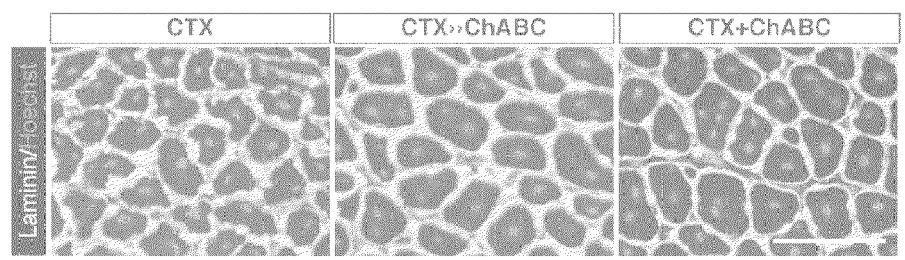
FIG. 2 is a figure (photograph) showing one example of the Laminin/Hoechst observation of the muscular fiber of the first mouse (CTX), second mouse (CTX>>ChABC), and third mouse (CTX+ChABC).

FIG. 2 is a figure showing one example of the Laminin/Hoechst observation of the muscular fiber in the first mouse (CTX), second mouse (CTX>>ChABC), and third mouse (CTX+ChABC). Note that the scale bar of white horizontal line at the lower left represents 100 μm.

Figure 3:
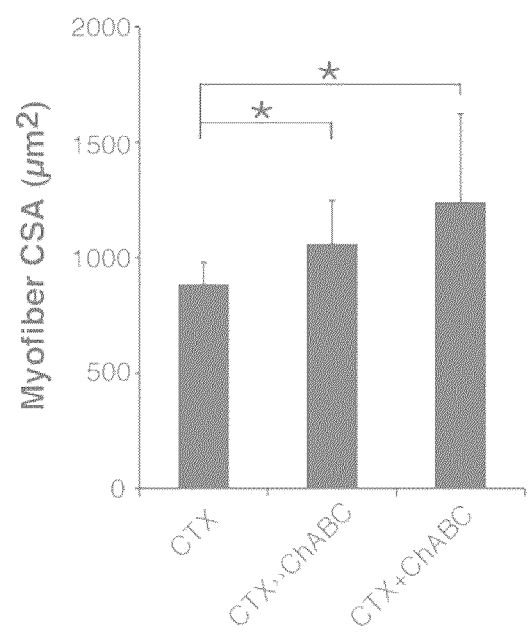
FIG. 3 is a bar chart showing one example of the cross-sectional area of the cell in the muscular fiber of the first mice (CTX), second mice (CTX>>ChABC), and third mice (CTX+ChABC).

FIG. 3 is a bar chart showing one example of the cross-sectional area of the cell in the muscular fiber of the first mouse (CTX), second mouse (CTX>>ChABC), and third mouse (CTX+ChABC). Note that * shown in FIG. 3 indicates P<0.01 in the t test.

In the Laminin/Hoechst observation of the muscular fiber of the above-mentioned first mouse (CTX), as shown in FIG. 2, it was observed that cells having central nucleus were closely packed without enlarging. It is thereby understood that, in response to the necrosis of the above-mentioned muscular fiber, the regeneration of such a muscular fiber occurs as usual by the administration of the above-mentioned CTX.

On the other hand, in the Laminin/Hoechst observation of the muscular fiber of the above-mentioned second mouse (CTX>>ChABC) and the above-mentioned third mouse (CTX+ChABC), as shown in FIG. 2, it is observed that the muscular fiber having the central nucleus enlarges. It is thereby understood that the regeneration and enlargement of the above-mentioned muscular fiber is enhanced by the administration of the above-mentioned ChABC.

Further, in the cross-sectional area of the cell in the muscular fiber of the above-mentioned first mouse (CTX), the above-mentioned second mouse (CTX>>ChABC), and the above-mentioned third mouse (CTX+ChABC), as shown in FIG. 3, it is perceived that the cross-sectional area of the cell in the muscular fiber of the above-mentioned second mouse (CTX>>ChABC) and the above-mentioned third mouse (CTX+ChABC) is significantly larger, as compared to the cross-sectional area of the cell in the muscular fiber of the above-mentioned first mouse. It is thereby understood that, upon the administration of the above-mentioned ChABC to the muscle of a model mouse of a muscle damage corresponding to muscular disorder, such a ChABC degrades chondroitin sulfate (CS) which inhibits the regeneration of the muscular fiber and enhances the regeneration and enlargement of such a muscular fiber.

Note that it is perceived that the cross-sectional area of the cell in the muscular fiber of the above-mentioned third mouse (CTX+ChABC) is, as shown in FIG. 3, significantly larger as compared with the cross-sectional area of the cell in the muscular fiber of the above-mentioned second mouse (CTX>>ChABC). Due to this, it is understood that the above-mentioned ChABC is more effective in the regeneration and enlargement of such a muscular fiber when administered simultaneously with the time point when the above-mentioned CTX was administered to the muscle, in other words, the time point when the necrosis of the muscular fiber by the above-mentioned CTX begins.

With regard to this, the inventors infer as follows: That is, in the above-mentioned third mouse (CTX+ChABC), the above-mentioned CTX penetrates into the inside of the above-mentioned muscular fiber and, at the same time, the administered ChABC penetrates into the inside of such a muscular fiber in conjunction with such a CTX, followed by instant degradation of chondroitin sulfate (CS) expressed on the periphery of such a muscular fiber. Due to this, a state in which the above-mentioned chondroitin sulfate (CS) is degraded is brought about at the time of the regeneration of the above-mentioned muscular fiber, which presumably prevents the inhibition of the regeneration of such a muscular fiber and enhances such a rate of regeneration.

(2-3) Pharmacological Test for Pharmacological Effects Using Model Mice of Myopathy Further, whether or not the administration of the skeletal muscle regeneration promoter according to the present invention to the muscle of the model mouse of myopathy enhanced a regeneration process of such a muscular fiber was examined.

As for a model mouse of the above-mentioned myopathy, the following method was employed. That is, it has been known that, in an mdx mouse which lacks the dystrophin protein on the membrane of the muscular fiber due to mutation of the dystrophin gene, the necrosis of its own muscular fiber begins to take place when three weeks pass after birth and, at the same time, the regeneration of the muscular fiber after the necrosis occurs (See, for example, Nonaka, I., "Lab. Anim. Sci. 48", 1998, p. 8-17). That is to say, the above-mentioned mdx mouse develops a myopathy of so-called Duchenne muscular dystrophy.

In view of this, using the above-mentioned mdx mouse as a mouse mode of a myopathy, whether or not the administration of the above-mentioned ChABC to such a mouse model of the myopathy enhanced a regeneration process of the muscle of such a mouse model of the myopathy was examined.

First, only 30 μL of ChABC of the above-mentioned predetermined concentration (2.0 IU/mL) was administered to the anterior tibialis muscle of the left hind limb of an mdx mouse (C57BL/10 lineage, equivalent to about 20 g, manufactured by CLEA Japan) at five weeks to six weeks after birth. Here, the dosage amount of the above-mentioned ChABC is 60 mIU per dose. Further, as a control experiment, only 30 μL of saline was administered to the anterior tibialis muscle of the right hind limb of the above-mentioned mdx mouse.

Then, using the mdx mouse at three days, seven days, or 14 days immediately after the administration of each formulation, a section of muscular fiber was prepared by the above-mentioned (1-1) to (1-3); and the fluorescence observation and imaging analysis were carried out.

Here, the above-mentioned Laminin/Hoechst observation was employed for the above-mentioned fluorescence observation; and the above-mentioned imaging analysis was used for the proportions of cells of the muscular fiber in which no central nuclei were present.

Figure 4:
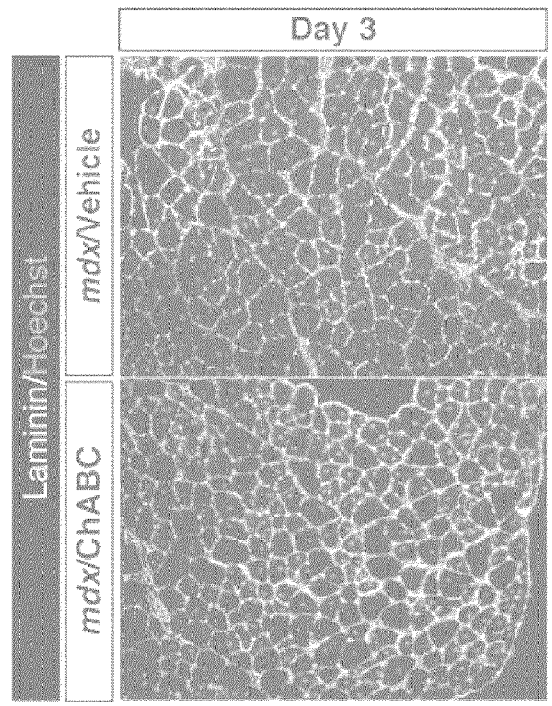
FIG. 4 is a figure (photograph) showing one example of the Laminin/Hoechst observation of the muscular fiber of an mdx mouse at three days after the administration of saline (vehicle) and ChABC.
Figure 5:
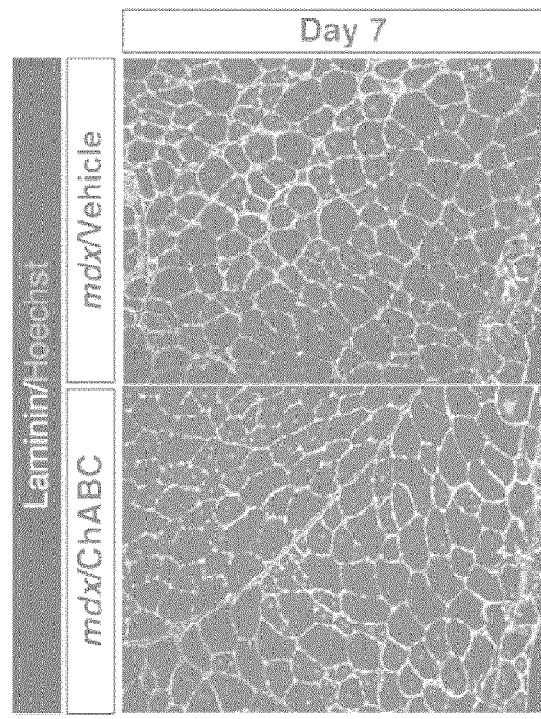
FIG. 5 is a figure (photograph) showing one example of the Laminin/Hoechst observation of the muscular fiber of an mdx mouse at seven days after the administration of saline (vehicle) and ChABC.
Figure 6:
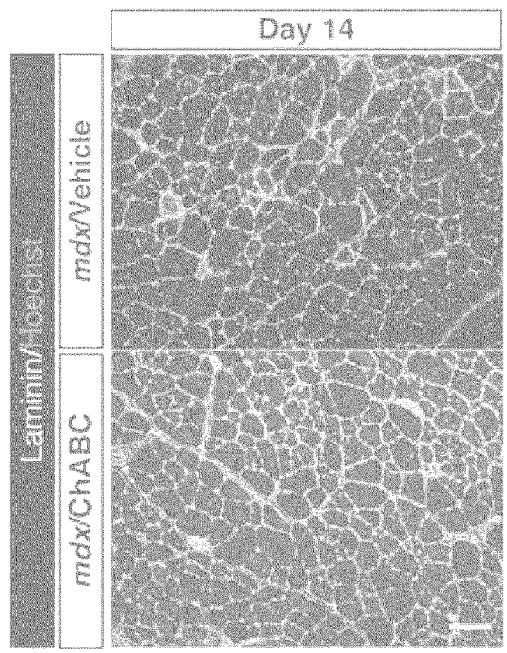
FIG. 6 is a figure (photograph) showing one example of the Laminin/Hoechst observation of the muscular fiber of an mdx mouse at 14 days after the administration of saline (vehicle) and ChABC.

FIG. 4 is a figure showing one example of the Laminin/Hoechst observation of the muscular fiber of mdx mouse at three days after the administration of saline (vehicle) and ChABC. Further, FIG. 5 is a figure showing one example of the Laminin/Hoechst observation of the muscular fiber of the mdx mouse at seven days after the administration of saline (vehicle) and ChABC. Further, FIG. 6 is a figure showing one example of the Laminin/Hoechst observation of the muscular fiber of the mdx mouse at 14 days after the administration of saline (vehicle) and ChABC. Note that FIG. 4 to FIG. 6 have the same magnification and the scale bar of white horizontal line at the lower left in FIG. 6 represents 100 μm.

Figure 7:
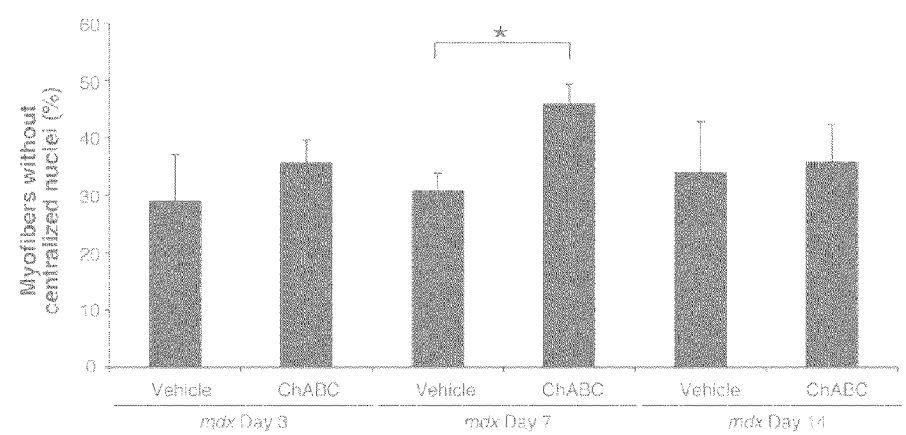
FIG. 7 is a bar chart showing one example of proportions of cells in which no central nuclei are present in the muscular fibers of mdx mice at three days, seven days, 14 days after the administration of saline (vehicle) and ChABC.

FIG. 7 is a bar chart showing one example of a proportion of cells in which the central nucleus is present in the muscular fiber of the mdx mouse at three days, seven days, 14 days after the administration of saline (vehicle) and ChABC. Note that * shown in FIG. 7 indicates P<0.005 in the t test.

In the Laminin/Hoechst observation of the muscular fiber of the mdx mouse at three days, seven days, or 14 days after the administration of the above-mentioned saline, as shown in FIG. 4 to FIG. 6, cells having the central nucleus were sparsely observed when any of three days, seven days, and 14 days passed. Further, the proportions of cells in which the above-mentioned central nucleus was not present were, as shown in FIG. 7, about 30% to about 40% when any of three days, seven days, and 14 days passed. It is thereby understood that cells of the muscular fiber of the above-mentioned mdx mouse repeat the necrosis and regeneration at a certain fixed frequency.

On the other hand, in the Laminin/Hoechst observation of the muscular fiber of the mdx mouse at three days, seven days, or 14 days after the administration of the above-mentioned ChABC, as shown in FIG. 4 to FIG. 6, it was observed that cells of the muscular fiber when seven days passed were the largest and most enlarged. Further, as for the proportion of cells in which the above-mentioned central nucleus was not present, as shown in FIG. 7, the proportion of cells in which the above-mentioned central nucleus was not present was about 50% when seven days passed, which was the highest. It is thereby understood that, when the above-mentioned ChABC is administered to the muscular fiber of the above-mentioned mdx mouse, the rate of regeneration of such a muscular fiber became higher than the rate of necrosis thereof and the regeneration and enlargement of such a muscular fiber is enhanced during a period of seven days immediately after the administration of such a ChABC. In other words, it is understood that the above-mentioned ChABC facilitates the regeneration of the muscular fiber in the myopathy and stabilizes such a muscular fiber (prevents the necrosis thereof).

It is to be noted that, as shown in FIG. 7, the proportion of cells in which the above-mentioned central nucleus in the muscular fiber in the mdx mouse at 14 days after the administration of the above-mentioned ChABC deceases, as compared with that in the muscular fiber of the mdx mouse when seven days pass. That is thought to be because the effect of the administration of the above-mentioned ChABC disappears. Meanwhile, it is perceived that the proportion of cells in which the above-mentioned central nucleus in the muscular fiber of the mdx mouse administered with the above-mentioned ChABC is, as shown in FIG. 7, higher in whole, as compared with the muscular fiber of the mdx mouse administered with the above-mentioned saline.

Due to this, the inventors are considering that, although the enhancement of the regeneration of the muscular fiber by the administration of the above-mentioned ChABC is effective only for a certain prescribed period, repeated administration of such a ChABC at a predetermined interval will make it possible to keep the enhancement of the regeneration of such a muscular fiber and thereby to facilitate the inhibition or delay of the necrosis of such a muscle of the myopathy.

Further, in the test example stated above, the pharmacological test for pharmacological effects of the above-mentioned ChABC was carried out by mainly employing mice as mammals. Yet, it is presumed that the same action and effect can be attained in other mammals, for example, human as well.

Further, the above-mentioned ChABC was employed as an enzyme degrading the above-mentioned chondroitin sulfate (CS) in the test example stated above. Yet, because the type of the enzyme degrading the above-mentioned chondroitin sulfate (CS) is not the determinant in light of principles, the same action and effect would be accomplished even when a chondroitinase such as, for example, chondroitinase AC, chondroitinase ACII, chondroitinase ACIII, chondroitinase B, chondroitinase C, or chondroitin sulfate ABC exolyase, is employed. Further, as long as it is an enzyme that concurrently has an activity of degrading the above-mentioned chondroitin sulfate (CS), that is, an enzyme that substantially degrades the chondroitin sulfate (CS), any enzyme including for example a hyaluronic acid-degrading enzyme such as HYAL-1 would be employed to accomplish the same action and effect.

Further, muscular dystrophy in the above-mentioned mdx mouse was employed as the above-mentioned myopathy in the test example stated above. Yet, because the type of the above-mentioned myopathy is not the determinant in light of principles, the same action and effect would be accomplished even when a myopathy including, for example, any of congenital or progressive muscular dystrophy, congenital or distal myopathy, myotonic dystrophy, myotonia syndrome, mitochondrial diseases, periodic paralysis, malignant hyperpyrexia, and ion channel diseases, is employed.

As just described, the skeletal muscle regeneration promoter according to the present invention is a skeletal muscle regeneration promoter that contains the enzyme degrading chondroitin sulfate (CS) as an active component and, when administered to the muscular fiber in muscular disorders or myopathies in mammals, enhances the regeneration of such a muscular fiber.

Thereby, upon the administration of the skeletal muscle regeneration promoter containing the above-mentioned enzyme to the muscular fiber in the above-mentioned muscular disorder or the above-mentioned myopathy, such an enzyme will degrade chondroitin sulfate (CS) that is present at the outer perimeter of the above-mentioned muscular fiber. Due to this, the inhibition of the regeneration of the muscular fiber by the above-mentioned chondroitin sulfate (CS) disappears, which makes it possible to enhance the regeneration and enlargement of such a muscular fiber. Further, the above-mentioned enzyme barely exhibits adverse effects on healthy muscular fibers that are not affected by either the above-mentioned muscular disorder or the above-mentioned myopathy and is thus highly safe. Because of this, the skeletal muscle regeneration promoter of the present invention is effective as a skeletal muscle regeneration promoter that restricts its target to the muscular fiber in the above-mentioned muscular disorder or the above-mentioned myopathy and is excellent in safety.

At the present day, in regard to the muscular disorder and myopathy, a stem cell therapy (for example, Naohiro Hashimoto, "Tanpakushitsu Kakusan Koso or Protein Nucleic Acid Enzyme 49", 2004, p. 741-748 or the like); a therapy using an inhibitor of myostatin which is derived from a cytokine having a function of suppressing muscle mass (for example, follistatin) (for example, Nakatani, M., and 11 others, "FASEB J. 22", 2008, p. 477-487 or the like); and studies therefor are actively developed, aiming at clinical application. It is considered that, when used in conjunction of those methods of treatment, the method of treatment using the skeletal muscle regeneration promoter according to the present invention (ChABC in the Example) turns out to be a more effective method of treatment for the muscular fiber in the above-mentioned muscular disorder or the above-mentioned myopathy.

Industrial Applicability

As described above, the skeletal muscle regeneration promoter according to the present invention is useful as a skeletal muscle regeneration promoter not only for common muscular disorders but also for myopathies such as muscular dystrophy and is effective as a skeletal muscle regeneration promoter capable of enhancing the regeneration of the muscular fiber in the muscular disorder or myopathy without affecting healthy muscular fibers.

What is claimed is:

1. A method for promoting skeletal muscle regeneration for muscular dystrophy comprising:
    administering to a muscular fiber of a subject in need thereof an effective amount of chondroitinase ABC, wherein said chondroitinase ABC, when administered into a muscular fiber of a mammal with muscular dystrophy, enhances regeneration of the muscular fiber.

2. The method according to claim 1, wherein said administering comprises injecting chondroitinase ABC into the muscular fiber.

3. The method according to claim 1, wherein said administration is combined with a treatment comprising any of a stem cell therapy and a therapy using an inhibitor of myostatin derived from a cytokine having a function of suppressing muscle mass.

* * * * *